United States Patent [19]

Turner et al.

[11] Patent Number: 4,498,904
[45] Date of Patent: Feb. 12, 1985

[54] DOSE METERING PLUNGER DEVICES FOR USE WITH SYRINGES

[76] Inventors: Robert C. Turner, 13 Belbroughton Rd., Oxford; Anthony B. Stone, 32 The Green, Charlbury, Oxford; Rury R. Holman, 42 Meadow Close, Farmoor, Oxford, all of England

[21] Appl. No.: 438,872
[22] PCT Filed: Feb. 12, 1982
[86] PCT No.: PCT/GB82/00034
§ 371 Date: Oct. 12, 1982
§ 102(e) Date: Oct. 12, 1982
[87] PCT Pub. No.: WO82/02662
PCT Pub. Date: Aug. 19, 1982
[51] Int. Cl.³ ............................................. A61M 5/00
[52] U.S. Cl. ..................................... 604/211; 604/224
[58] Field of Search ............... 604/211, 208, 209, 210, 604/218, 224; 222/46, 48, 390, 308, 309

[56] References Cited

U.S. PATENT DOCUMENTS

| 2,129,675 | 9/1938 | Cole | 604/211 |
| 3,141,583 | 7/1964 | Mapel et al. | 222/309 |
| 3,232,117 | 2/1966 | Gilmont | 604/211 |
| 3,481,510 | 12/1969 | Allen | 222/79 |
| 4,194,505 | 3/1980 | Schmitz | 604/211 |
| 4,244,366 | 1/1981 | Raines | 604/211 |
| 4,367,739 | 1/1983 | Le Veen et al. | 604/224 |

FOREIGN PATENT DOCUMENTS 1070784 12/1959 Fed. Rep. of Germany .
7246823 7/1974 France .

OTHER PUBLICATIONS

"Convenient Pocket Insulin Syringe", John S. Paton et al., The Lancet, 24th Jan. 1981.

Primary Examiner—John D. Yasko
Attorney, Agent, or Firm—Oblon, Fisher, Spivak, McClelland & Maier

[57] ABSTRACT

A dose metering device for use with a syringe comprises a fixed screwthreaded member (17) which is either integral with or fixed in use to the cylinder (10) of the syringe and is in threaded engagement with a screwthreaded plunger (13) which can be rotated by a manually-rotatable cap (30) acting through a ratchet and pawl mechanism (32, 34) whose ratchet wheel (26) drives a driving rod (24) which is slidably keyed to the plunger (13). The plunger engages the piston or plug (11) of the syringe. A stop (42) limits rotation of the cap (30) which can be turned away from the stop through a variable angle to a selected angular position shown on a scale (39) of volumetric dose units, the pawl (32) overriding the ratchet teeth (34), to preset a dose to be expressed. The cap (30) can then be turned back to the stop, rotating the plunger (13) via the ratchet and pawl mechanism and causing the plunger to advance the syringe piston or plug (11) through a corresponding axial distance so as to express a metered dose, corresponding to the setting preset on the scale, from the syringe. A succession of preset doses, of the same or different volumes can thus be expressed from the syringe until it is empty. The syringe may employ a prefilled ampoule (50B) of dose liquid which is sealed by a sliding plug (11B) engaged in use by the screw plunger (13B).

44 Claims, 21 Drawing Figures

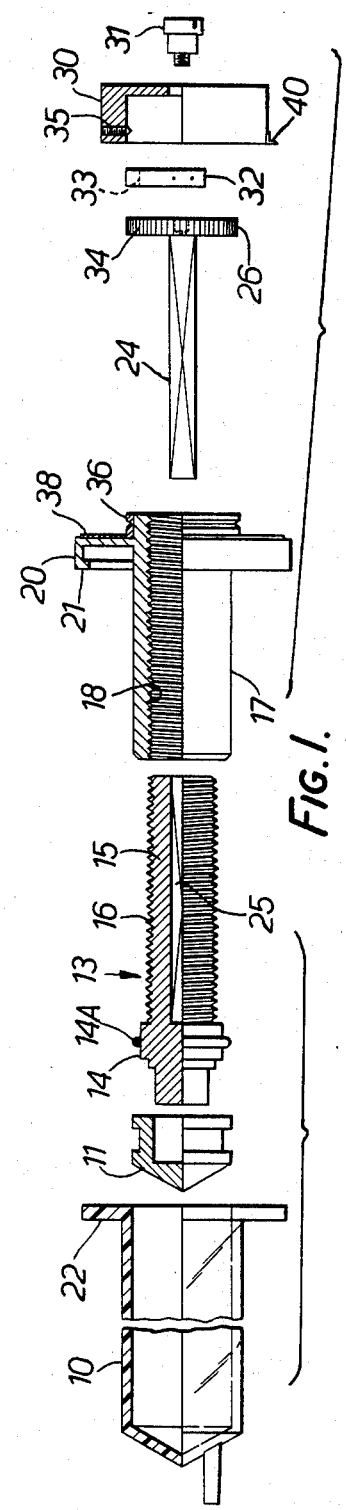
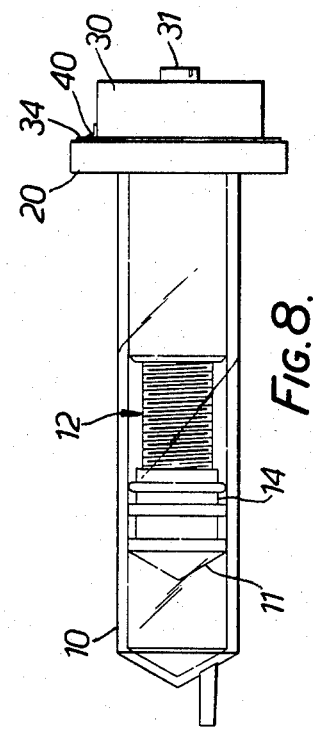
Fig. 1.
Fig. 8.

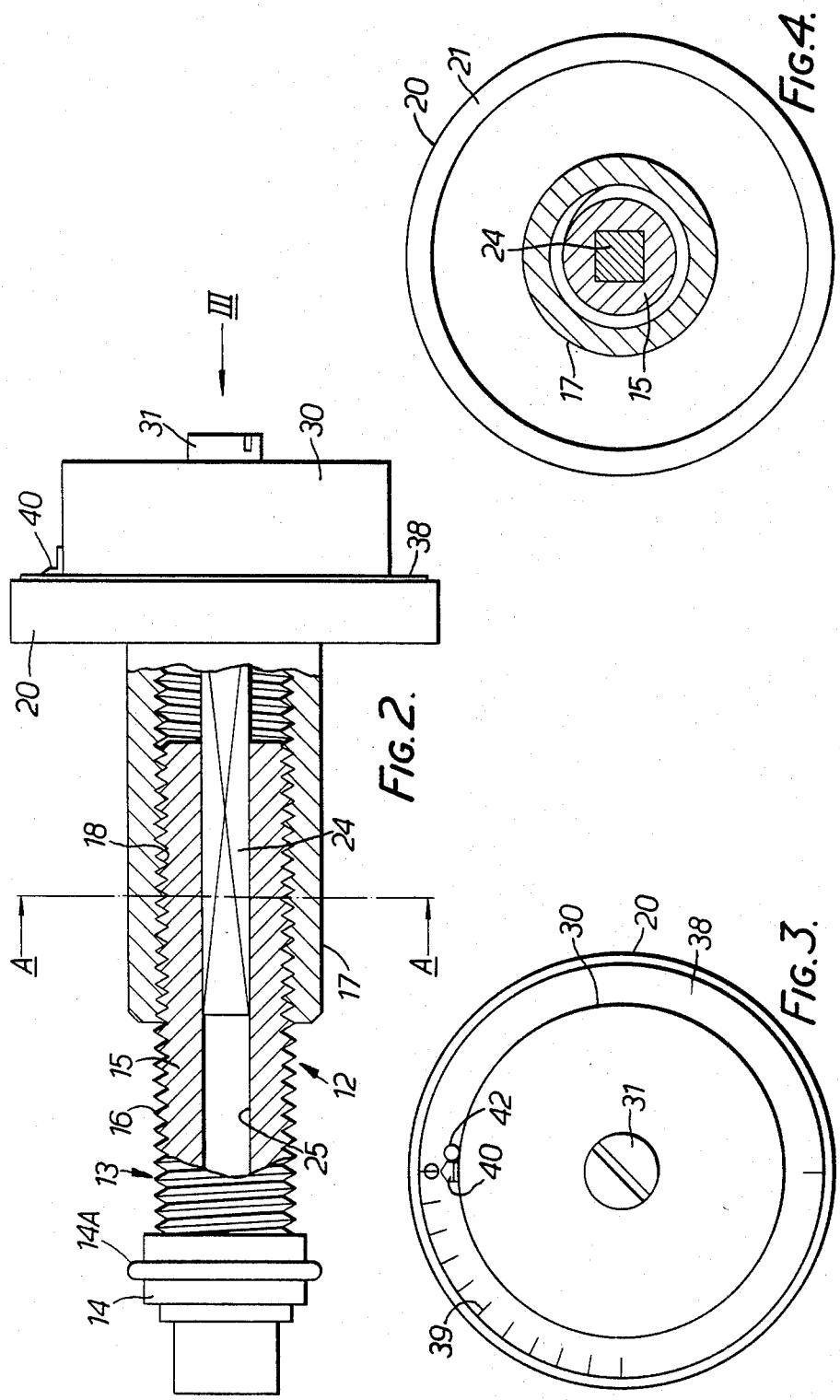

DOSE METERING PLUNGER DEVICES FOR USE WITH SYRINGES

This invention relates to syringes, and to a dose metering device for use in conjunction with a syringe in place of the conventional manually-depressible plunger thereof.

The invention is particularly although not exclusively applicable to medical syringes for delivering doses of liquid, for example hypodermic syringes for injecting drugs in liquid form, such as insulin. Diabetics require to inject themselves repeatedly with insulin, and as each injection often has to be of a different amount from the last, it is necessary to draw up each injection dose separately from a multi-dose container into a syringe, check the amount in the syringe and then inject the dose.

It is an object of the present invention to provide a syringe with a dose-metering device which can be used to inject successive metered doses of the same or different preset volumes from the filled syringe. Whilst the invention is of particular application in connection with the injection of insulin, it may have other uses too, such as the metered delivery of a parenteral anaesthetic or analgesic, or of small variable doses of liquid in laboratories or factories.

According to the present invention, from one aspect, a dose metering device for a syringe comprises an axially movable plunger which in use drives the piston of the syringe to express a dose of fluid therefrom, the plunger being movable in successive axial steps of variable length by a rotary screw mechanism driven by successive respective operating strokes of corresponding length of a manual operating member whereby successive doses whose volumes correspond to the lengths of the respective operating strokes of the operating member will be expressed from the syringe, and the operating member acting through a unidirectional coupling which permits its retraction after each operating stroke to a starting point for the next stroke, and in which the length of each operating stroke of the operating member can be variably preset thereby presetting the volume of the corresponding dose.

The operating member is rotatable and effects angular operating strokes which are converted by the screw mechanism into corresponding axial steps of the plunger, and the presetting of the lengths of the operating strokes of the operating member is performed by selectively varying the angular position of the starting point of each operating stroke, the end of each stroke being determined by stop means.

The device includes scale means, for example an arcuate scale, preferably calibrated in volumetric units, and a cooperating pointer, preferably arranged to that the volume of each dose to be expressed, corresponding to the angle through which the operation member is rotated, can be directly indicated and pre-set on the scale.

In one construction, the operating member is coupled through the unidirectional coupling to a rotary screw mechanism, the selection of the starting point of each operating stroke being performed by rotating the operating member in the direction of retraction to its selected starting point on the scale. The screw mechanism may comprise an external helical screwthread formed coaxially on the plunger and a cooperating internal helical screwthread formed coaxially in the cylinder of the syringe or in a tubular part which in use is fixed to the cylinder.

The unidirectional transmission may conveniently comprise a ratchet and pawl mechanism.

Thus prior to each dose expression, the operating member is preset by being moved from the zero mark to the scale marking corresponding to a required dose size, the pawl riding over the tips of the ratchet teeth so that the plunger is not rotated. Then when the dose expression is required, the operating member is manually turned back through one operating stroke to the zero mark to engage the stop means, this movement driving the plunger via the ratchet mechanism and causing the preset, metered dose to be expressed from the syringe.

The piston may take the form of a sliding plug in the syringe cylinder by which a quantity of liquid to be expressed in successive doses can be trapped in the cylinder, the sliding plug being engaged by the plunger of the dose metering device. The arrangement can be such that the device can be utilized repeatedly with a succession of prefilled syringe bodies, each sealed by its sliding plug piston and each adapted to be thrown away, or refilled, when empty.

Alternatively the liquid to be expressed, instead of being filled directly into the cylinder of the syringe, could be pre-filled into a separate sealed ampoule which is adapted to be fitted into the syringe cylinder and from which the liquid can be expressed by the action of the plunger; the ampoule may have a membrane portion of its wall adapted to be pierced by a needle in the syringe cylinder when it is inserted therein to allow the liquid to be expressed.

For example the piston may take the form of a sliding plug inserted into the end of the tubular body of the ampoule to seal the liquid therein and slidable inwardly in the ampoule body to cause the expression of the liquid. The membrane of such an ampoule would be at the opposite end of its tubular body, the syringe cylinder having a tubular needle mounted to project into the syringe interior so as to pierce the membrane when the ampoule is pushed fully home into the syringe cylinder, the liquid being expressed through the tubular needle when the plunger device is operated.

The invention comprises not only the dose-metering device in any of its forms as a separate component, but also a syringe having such a device, either detachably mounted on the cylinder or integrated with the syringe.

For example, the internal screwthread may be formed on an integral tubular extension of the cylinder of the syringe.

In such an arrangement the operating member may comprise a sleeve rotatably mounted on the said tubular extension and slidable thereon between first and second axial positions, a stop being mounted on the said extension and cooperating with an abutment on the sleeve to limit rotation of the sleeve when the sleeve is in the first axial position, sliding movement of the sleeve into the second axial position moving the abutment surface clear of the stop so that the stop no longer hinders rotation of the sleeve.

Conveniently, the sleeve may be arranged to be held in its first position by an ampoule inserted into the cylinder of the syringe, and to be free to move into its second position when the ampoule is removed from the cylinder.

In another construction, the operating member may comprise a sleeve slidably mounted on the cylinder of the syringe and rotatable thereon, when in an operative position thereon, to drive the plunger, the sleeve being releasably retained against axial movement out of its operating position on the sleeve by a spring catch. Conveniently the spring catch is held in engagement by an ampoule when inserted into the cylinder, and is resiliently self-released when the ampoule is removed from the cylinder.

The invention may be carried into practice in various ways, but three specific embodiments thereof will now be described by way of example only and with reference to the accompanying drawings, in which:

FIG. 1 is an exploded view of a first embodiment of a syringe provided with a dose metering device in accordance with the invention;

FIG. 2 is a part-sectional side view of the dose metering device of FIG. 1;

FIG. 3 is an end view as seen in the direction of the arrow III in FIG. 2;

FIG. 4 is a cross-section on the line A—A in FIG. 2;

FIG. 8 shows the assembled syringe of FIG. 1, with the metering device inserted in its cylinder;

Figure 5:
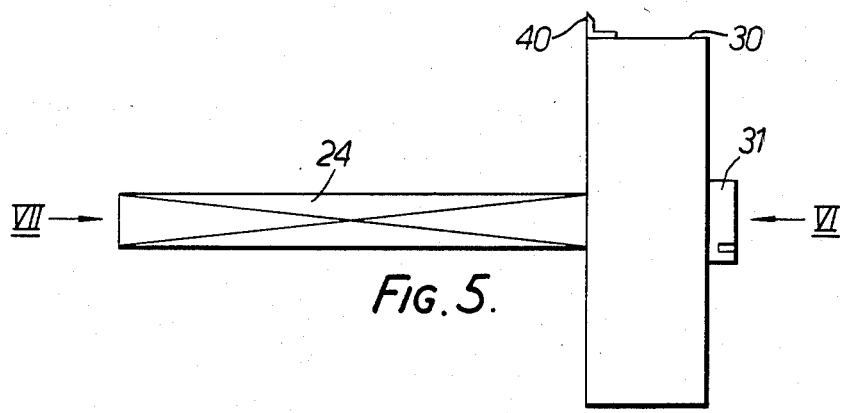
FIGS. 5, 6 and 7 are respectively a side view of the head assembly of the metering device of FIG. 2 and end views thereof as seen in the directions of the arrows VI and VII respectively.

The syringe shown in FIGS. 1 to 8 comprises a transparent or translucent tubular body 10 of conventional form, referred to as the cylinder of the syringe, to which a needle may be fitted for injection purposes if desired. Although in this case the cylinder 10 is of circular cross-section, this is not essential. Instead of the usual manually-depressed plunger, the cylinder 10 has a sliding plug 11 which fits in its interior and seals off a quantity of liquid in the cylinder for expression in metered doses.

The dose metering device 12 is shown in assembled form in FIGS. 2 to 4, and can be inserted into the interior of the cylinder 10 behind the plug 11 as shown in FIG. 8. The device 12 includes a plunger 13 having a head 14 at one end and having a tubular body 15 integral with the head and provided with an external screwthread 16. The device 12 also includes a cooperating sleeve 17 (called the fixed sleeve 17) formed with an internal screwthread 18 which matches the thread 16 so that the two parts 15 and 17 can be telescopically overlapped with their threads 16 and 18 inter-engaged, as shown in FIG. 2. The screwthreads 16 and 18 are shown diagrammatically only in FIGS. 1, 2 and 8, and will in many cases be of much coarser pitch than indicated, depending on the size range of doses to be expressed. When the device 12 is fully inserted in the cylinder 10, the head 14 engages behind the sliding plug 11, and withdrawal of the assembly 15, 17 from the cylinder 10 is prevented, for example by means of an integral clip 20 on the head of the sleeve 17, the clip 20 having an inturned lip 21 which snaps behind a flange 22 on the cylinder 10. Moreover the clip 20 cooperates with a flat or flats (not shown) on the circumferential edge of the flange 22 to prevent rotation of the sleeve 17 when the device 12 is fully inserted into the cylinder 10. Instead of the clip 20, various other means may be devised for ensuring that the sleeve 17 cannot rotate relative to the cylinder 10 nor be pushed out of the cylinder 10 by the reaction of the cooperating screwthreads 16 and 18 when the plunger 13 is rotated in use as will now be described. A driving rod 24 with a ratchet head 26 is provided for rotating the plunger 13, the rod 24 being of square (or other non-circular) cross-section and engaging slidably in a bore 25 of corresponding cross-section in the body 15 of the plunger 13 as shown best in FIG. 4. An operating cap 30 is rotatably secured by a screw 31 on the ratchet head 26 of the driving rod, and carries in its interior a pawl 32 in the form of a spring strip having an inturned end 33 which constitutes the tooth of the pawl and cooperates with the external ratchet teeth 34 of the head 26 (see FIG. 7).

Figure 6:
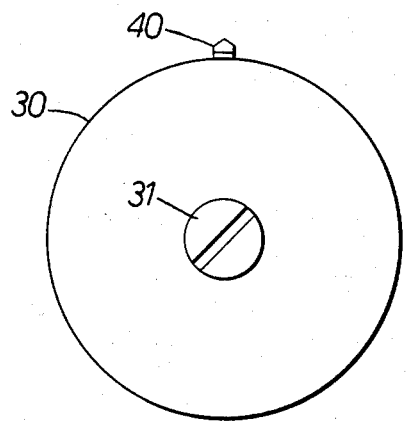
Figure 7:
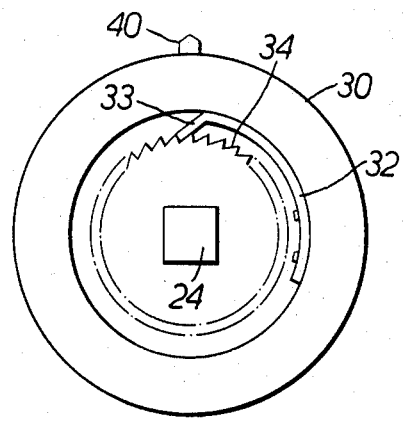

With the metering device 12 inserted fully in the cylinder 10, the cap 30 can then be rotated manually in the anti-clockwise direction as seen in FIGS. 3 and 6 but will not rotate the plunger body 15 because the pawl 32 will ride over the ratchet teeth 34. The friction between the cooperating screwthreads 16 and 18 is arranged to be sufficiently greater than the friction between the pawl 32 and ratchet teeth 34 during such anti-clockwise rotation of the cap 30, so that the plunger body 15 is not rotated. Alternatively or in addition, the plunger body 15 can be frictionally prevented from rotation when the cap is turned by a sealing ring 14A on the plunger head 14, which engages the cylinder 10, although an air vent will be required to prevent the sealing ring 14A from trapping air between the plug 11 and the plunger head 14 and hence moving the plug 11, during insertion and removal of the device 12.

When the cap 30 is rotated in the opposite direction, the pawl 32 will engage behind one of the ratchet teeth 34 and cause the rod 24 to rotate the plunger body 15, the cooperating screwthreads 16 and 18 acting as a lead-screw to advance the rotating plunger 13 axially inwardly and depress the sliding plug 11 in the cylinder. As mentioned, the clip 20 prevents the sleeve 17 from being pushed away from the cylinder 10 during this operation.

An annular indicating disc 38 marked with a scale 39 of volumetric dose units is mounted on the head of the sleeve 17 between the cap 30 and the clip 20. The disc 38 may be formed as an integral part of the head of the sleeve 17. The cap 30 is retained against axial withdrawal from the sleeve 17 by means of small screws 35 which project radially inwardly through holes in the wall of the cap and engage in a circumferential groove formed on the hub 36 of the indicating disc 38. The cap 30 carries a pointer 40 which cooperates with the scale 39. When the cap 30 is rotated clockwise in FIG. 3 into the position shown in which the pointer 40 registers with the zero mark on the scale 39, further clockwise rotation of the cap 30 is prevented by the engagement of the pointer 40 with a stop 42 removably screwed into the indicating disc 38 adjacent to the zero on the scale 39.

Thus in use, a quantity of fluid to be dispensed, for example insulin to be injected in metered doses, is introduced into the cylinder 10 and the sliding plug 11 is inserted to trap the fluid. The plunger 13 is screwed fully into the interior of the fixed sleeve 17 with the stop 42 removed to allow free rotation of the cap 30 relative to the sleeve 17, and the stop 42 is then screwed back into its operative position on the scale 39. The dose metering device 12 is then inserted into the cylinder 10, and is pushed fully home until the clip 20 is engaged with the cylinder flange 22. The syringe is now ready for use.

To set the size of the dose to be dispensed or injected, the cap 30 is first rotated (anti-clockwise as seen in FIG. 3) until the pointer 40 reaches the index mark on the scale 39 which corresponds to the required dose. This rotation will not drive the plunger 13 because the pawl 32 will ride over the ratchet teeth 34. To dispense or inject the dose which has been preset in this way, the cap is now turned manually in the clockwise direction in FIG. 3 until the pointer reaches the zero mark and the stop 42 prevents further rotation of the cap. This rotation causes the plunger 13 to be rotated through a corresponding angle by the ratchet and pawl mechanism, while at the same time the plunger will be advanced axially through a corresponding distance by the cooperation of the screwthreads 16 and 18, driving the plug 11 inwardly to express the metered dose of fluid from the cylinder. If a needle is fitted to the syringe the metered dose can be injected subcutaneously.

The operation can be repeated successively to dispense successive metered doses of the same or different sizes, each having been preset by the rotation of the cap to the required index setting on the indicating scale, until the syringe is empty, when it can be refilled for further use. Alternatively, the empty syringe could be thrown away and replaced by another prefilled syringe whose liquid charge is retained by its plug 11, the dose metering device 12 being inserted into the cylinder of the replacement syringe prior to use, after the plunger 13 has been screwed back into the sleeve 17 as described above.

Whilst in the embodiment of FIGS. 1 to 8 the stop 42 for the pointer is removably secured to the threaded leadscrew sleeve 17 and has to be removed from the sleeve before the plunger 13 can be screwed back fully into the sleeve at the conclusion of a series of dose expressions, other arrangements are possible. For example, the stop engaged by the pointer may be carried by the cylinder of the syringe itself, for example as a part of a bayonet connection for the non-rotary leadscrew member. In that case the metering device would simply be removed from the cylinder of the syringe prior to the screwing back of the plunger, so that the stop on the cylinder would no longer hinder reverse rotation of the plunger.

As described, the syringe of FIGS. 1 to 8 is designed to be filled directly with the dose liquid. FIGS. 9 to 14 show a second embodiment of the invention in which the dose liquid is pre-filled into a separate ampoule and sealed therein by a sliding plug. The prefilled ampoule can be inserted into the cylinder of the syringe and pushed home until a membrane sealing the inner end of the ampoule is pierced by a tubular needle in the cylinder, and the dosing device can then be operated to cause its plunger to drive the sliding plug inwardly in the ampoule to express a pre-set metered dose of liquid through the tubular needle.

Moreover, whereas in the embodiment of FIGS. 1 to 8 it is necessary to unscrew and remove the stop 42 before the plunger of the leadscrew mechanism can be screwed back into the fixed sleeve for re-use of the device, in the embodiment of FIGS. 9 to 14 no such removal of a stop is necessary.

In FIGS. 9 to 14, parts which correspond to parts of the embodiment of FIGS. 1 to 8 are given the same reference numerals as therein but qualified by the letter B. Thus in the embodiment of FIGS. 9 to 14, the syringe body or barrel 10B can receive in its interior a cylindrical ampoule 50B prefilled with a quantity of the dose liquid sufficient for several doses, the ampoule being sealed by a sliding plug 11B inserted into one open end of its tubular body to retain the liquid therein. At its other end the ampoule 50B is formed with a protruding neck 51B over the mouth of which a pierceable membrane 52B is secured by means of a resilient retaining cap 53B. The open lower end of the barrel 10B, as seen in FIG. 10C, receives the ampoule 50B, and is formed with an internal screwthread, into which is screwed an externally-threaded needle-mounting plug 56B of plastics material whose wall 57B supports a double-ended tubular needle 58B. One end of the needle 58B projects forwardly of the plug 56B for subcutaneous dose injection purposes, whilst the other end projects inwardly into the interior of the syringe cylinder 10B when the plug 56B is screwed into the cylinder 10B. A protective outer cap 59B is a press fit onto the plug 56B to enclose and guard the needle, and can be removed manually to expose the latter for use. The ampoule 50B is an easy sliding fit in the interior of the barrel 10B, and when it is pressed fully home against a reset washer 92B of the syringe as will be described, and the plug 56B is screwed fully home into the barrel, the membrane 52B of the ampoule will be pierced by the inner end of the tubular needle 58B which will penetrate into the interior of the ampoule to allow liquid therein to be expressed through the needle for injection purposes. The membrane 52B can be removed after use and replaced by an intact membrane if it is desired to refill the ampoule rather than throwing it away. The ampoule itself may be made of any suitable plastics or other material, and is preferably transparent or translucent, and the membrane 52B may be of rubber or plastics or other suitable pierceable sheet material. The sliding plug 11B is preferably of rubber or synthetic rubber, although it also may be made of some other suitable material. The needle 58B and its mounting cap 59B may be disposable.

The dose metering mechanism in this embodiment comprises a leadscrew mechanism formed by a pair of cooperating screwthreaded members 13B and 17B. The member 17B comprises the left-hand part of the syringe barrel 10B and is formed with an internal screwthread 18B, and the member 13B is a rotatable plunger with an external screwthread 16B which is screwed into the threaded bore of the barrel portion 17B. The plunger 13B has a splined unthreaded bore 25B which slidably receives a rotatable grooved driving rod 24B of corresponding section which can be turned in one direction about its longitudinal axis by an operating cap 30B acting through a ratchet mechanism 32B, 34B, the ratchet teeth 34B being formed on a ratchet cylinder 26B carried by the driving rod 24B.

The general arrangement and operation of the ratchet mechanism is much as in the embodiment of FIGS. 1 to 8, and will be described in more detail below.

Figures 9, 10A:
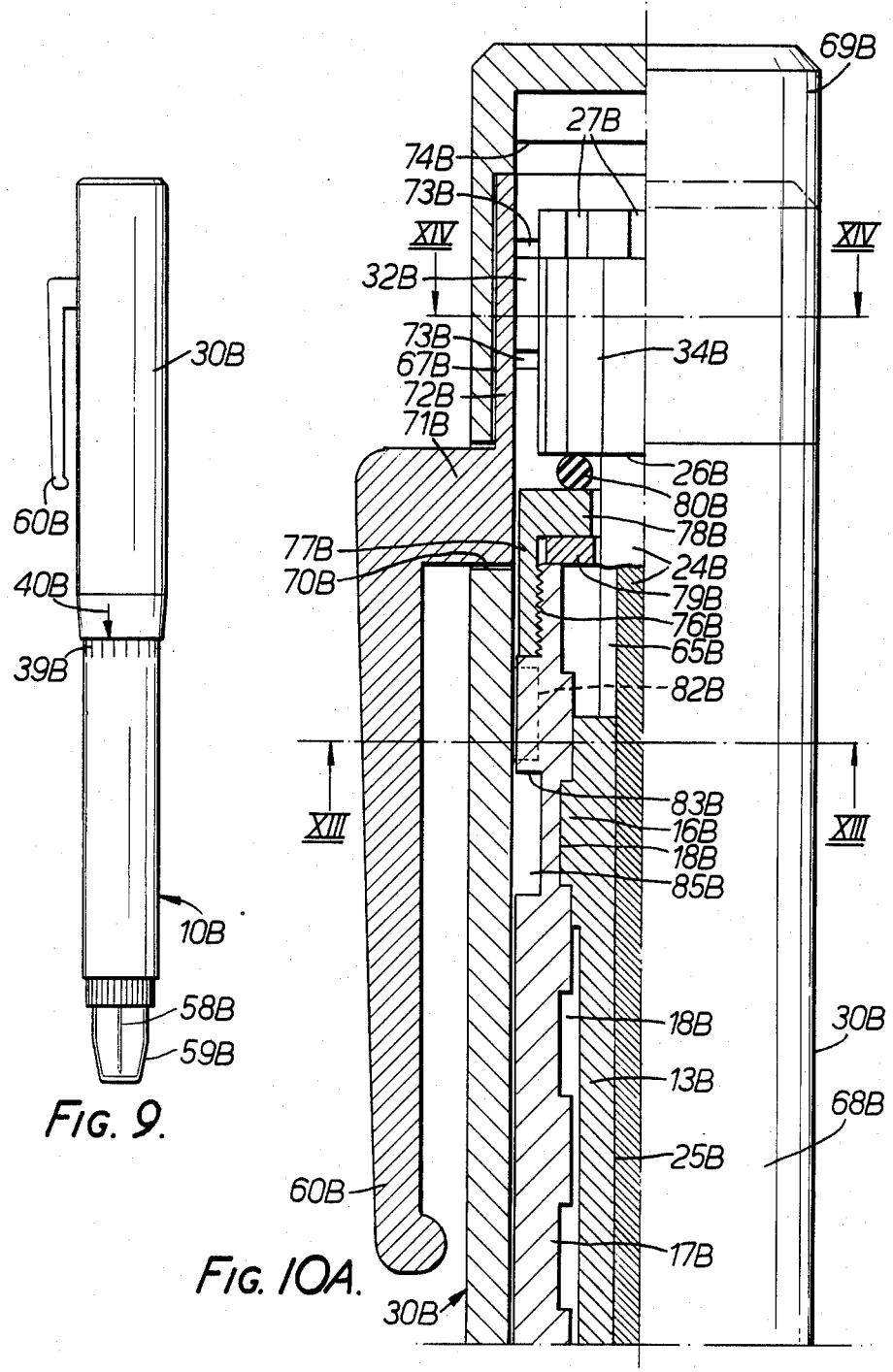
FIG. 9 is a side view of a second embodiment of the invention comprising a syringe employing a disposable ampoule of dose liquid.
FIGS. 10A, 10B and 10C are half-sectioned views on a larger scale of the syringe of FIG. 9.

FIG. 9 shows the overall external shape of the syringe of this embodiment, which resembles that of a pocket pen, having the barrel 10B referred to which is adapted to receive an ampoule 50B through its right-hand end, as seen in FIG. 9, the operating cap 30B being mounted on the left-hand end portion 17B of the barrel in a non-detachable manner but being rotatable relatively to the barrel and being telescopically slidable axially thereon through a limited distance. The cap 30B is provided with a clip 60B for retaining the syringe in a coat pocket. At its said right-hand end the barrel is provided with the push-on protective cap 59B to protect the needle 58B.

As mentioned, the barrel portion 17B is formed with an internal coarse-pitch helical screwthread 18B extending over nearly the whole length of the barrel portion 17B. The cooperating thread of the plunger 13B is a short length of coarse-pitch external screwthread 16B formed on the head only of the plunger, the reduced-diameter main body portion of the length of the plunger being smooth and unthreaded. The thread 16B is in this case 7 mm in overall diameter and 0.02 inch (0.5 mm) deep. The thread 18B corresponds in diameter and depth, and the pitch of both threads 16B and 18B is 9 mm. The end of the plunger 13B remote from its thread 16B is adapted to enter the open end of an ampoule 50B inserted into the syringe and to abut against its sliding plug 11B, for expressing liquid from the syringe by rotation of the cap 30B. The driving rod 24B for the plunger 13B is of circular cross-section and is formed with a longitudinal groove 65B (FIGS. 12 and 13) in its external surface extending over substantially its whole length. The driving rod 24B is a sliding fit in the bore of the plunger 13B, and relative rotation between the rod 24B and the plunger 13B is prevented by a single integral internal longitudinal spline 66B in the bore of the plunger 13B which keys into a single longitudinal groove 65B of the driving rod 24B, thus permitting longitudinal sliding movement between the rod 24B and the plunger 13B. The driving rod 24B carries a ratchet cylinder 26B formed around its circumference with sixteen equally-spaced axially-extending ratchet teeth 34B. The cooperating pawl 32B forms part of a metal clip fitting 67B carried by the upper cap 30B, as will be described. Thus rotation of the cap 30B on the barrel 10B, in the clockwise direction as seen in FIG. 14, causes the pawl 32B to turn the ratchet cylinder 26B and the driving rod 24B, which rotates the plunger 13B of the leadscrew mechanism so that the plunger 13B moves a corresponding axial distance downwardly in FIGS. 10A and 10B, depressing the plug 11B in an ampoule 50B inserted in the barrel 10B to express liquid from the syringe. A scale 39B of dose units is marked around the outer circumference of the barrel 10B adjacent to the rim of the cap 30B, and cooperates with an index mark 40B on the cap which constitutes the pointer.

The cap 30B is formed in two parts, namely a lower open-ended tubular part 68B and an upper cup-shaped closure member 69B which is suitably bonded, as by adhesive, to the upper end of the part 68B. A recess 70B is formed at the upper end (as seen in FIG. 10A) of the part 68B, in which recess the stalk 71B of the metal clip 60B is trapped by the closure member 69B. The stalk 71B is rigidly secured to a cylindrical metal sleeve 72B also forming part of the clip fitting 67B, the sleeve 72B being formed with two arcuate recesses 73B which define between them the pawl 32B, the latter being an integral part of the sleeve 72B and being bent inwardly within the sleeve for cooperation with the ratchet teeth 34B. It will be seen that the axial length of the ratchet cylinder 26B is more than twice the width of the pawl 32B, to allow the cap 30B to be moved axially relative to the barrel 10B through a short distance without decoupling of the ratchet 34B and pawl 32B, as will be described. The upper end face of the ratchet cylinder 26B is formed with radial grooves or serrations at 27B, for frictional engagement by cooperating formations 74B on the inner end face of the cup-shaped closure member 69B when the cap 30B is depressed downwardly along the barrel.

As shown in FIG. 10, the upper part 17B of the barrel 10B is formed on its outer circumference with an external screwthread 76B onto which an internally-threaded retaining sleeve 77B is screwed, the sleeve having a radially-inwardly-directed flange 78B which overlies the head of the plunger 13B, a washer 79B being interposed between the flange 78B and the upper rim of the barrel portion 17B. A resilient O-ring 80B surrounds the driving rod 24B, which extends through the sleeve 77B and washer 79B into engagement in the splined bore of the plunger 13B. The resilient O-ring 80B, which is made for example of rubber, is interposed between the ratchet cylinder 26B and the flanged sleeve 77B. The washer 79B is crimped to or otherwise secured against sliding on the driving rod 24B whilst allowing the driving rod to rotate, and by its engagement under the flange 78B of the sleeve 77B it serves to hold down the driving rod 24B and the ratchet cylinder 26B and to hold the O-ring 80B in permanent axial compression between the ratchet cylinder and the insert 77B.

Figure 12:
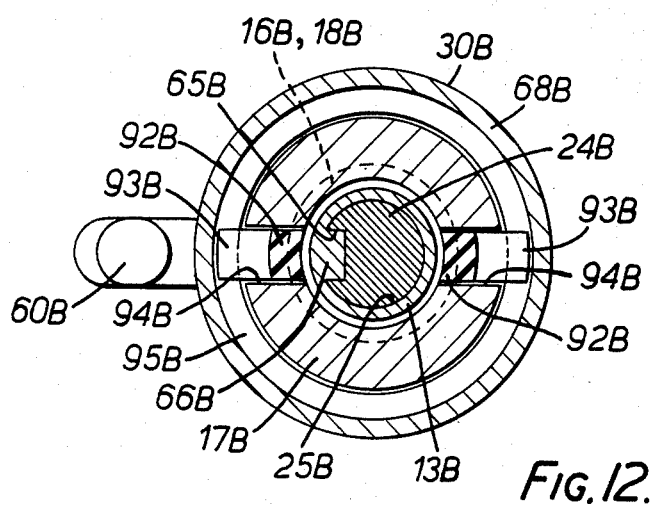
FIGS. 12, 13 and 14 are views in cross-section on the lines XII—XII, and XIII—XIII and XIV—XIV respectively of FIGS. 10B and 10A respectively.
Figure 13:
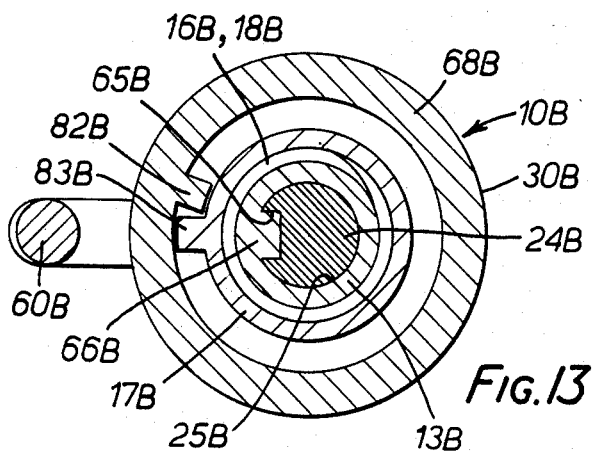
Figure 14:
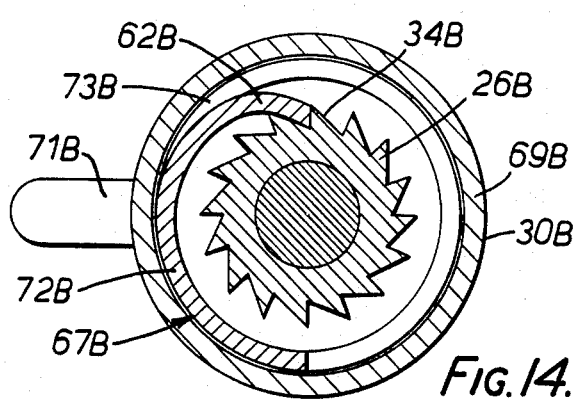

To limit the rotation of the cap 30B in the clockwise direction as seen in FIG. 14 (and the anticlockwise direction as seen in FIGS. 12 and 13) the cap 30 is formed with a radially-inwardly-directed internal lug 82B which is integral with the sleeve portion 68B of the cap and which cooperates with a radially-outwardly-projecting external lug 83B formed as an integral part of the barrel portion 17B on its outer circumferential surface. With the cap 30B fully retracted on the barrel 10B, as shown in full lines in FIGS. 10A and 10B, the lug 82B on the cap engages the side of the lug 83B on the barrel, as shown in FIG. 13, when the cap is rotated (clockwise in FIG. 14) to its limiting position in which the pointer 40B registers with the zero mark on the scale 39B.

It will be appreciated however that in its retracted position on the barrel 10B the cap 30B cannot be rotated in the anticlockwise direction in FIG. 14 through a full 360° because the lug 82B will come into engagement with the other side of the lug 83B and prevent further anticlockwise rotation. For this reason provision is made for depressing the cap 30B along the barrel 10B into the position shown in broken lines in the right-hand side of FIGS. 10A and 10B, in which position the lug 82B will have passed into the annular space 85B below the lug 83B and between the barrel portion 17B and the wall of the cap 30B, and the cap can be rotated freely through as many complete turns as required because the lug 83B is clear of the path of the lug 82B. In this lower position, moreover, the pawl 32B will still be in engagement with the ratchet teeth 34B at the lower part of the ratchet cylinder 26B.

Figures 10B, 10C:
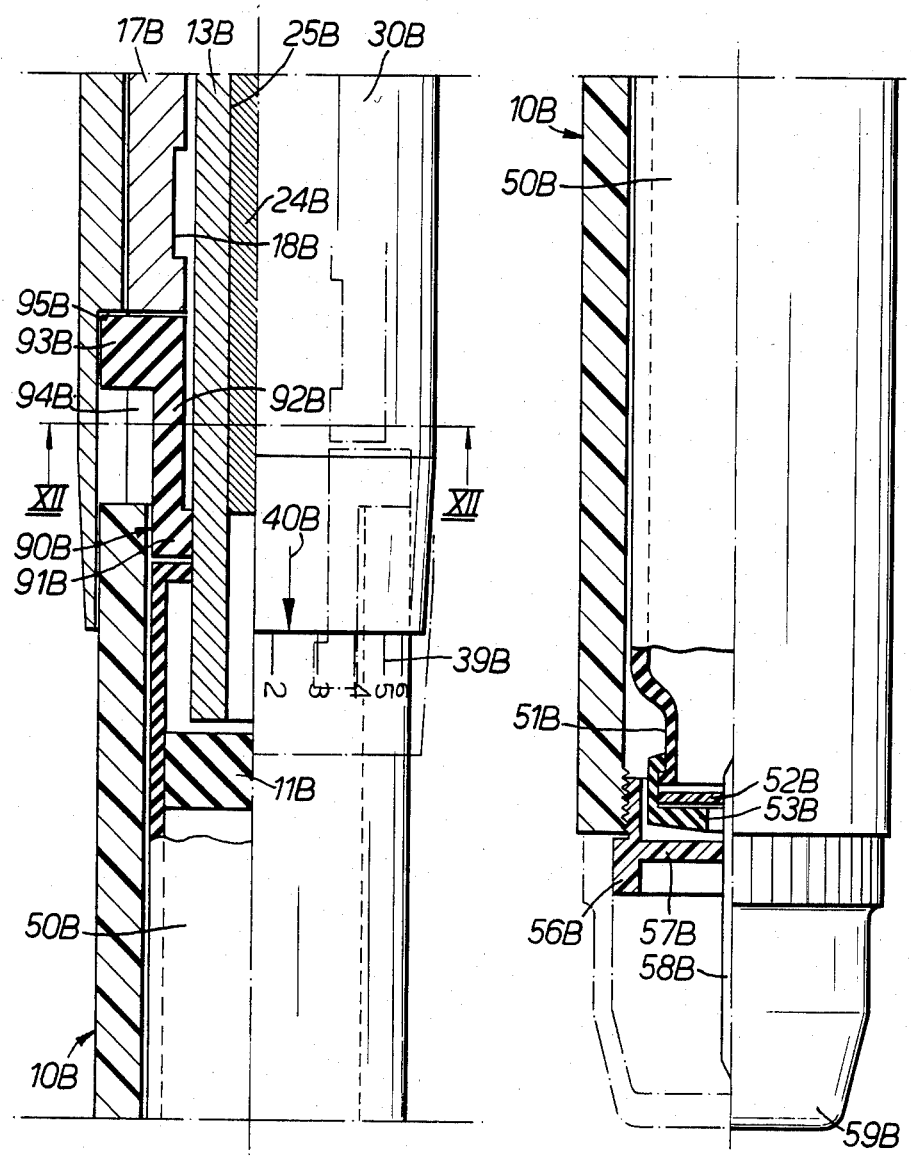
Figure 11:
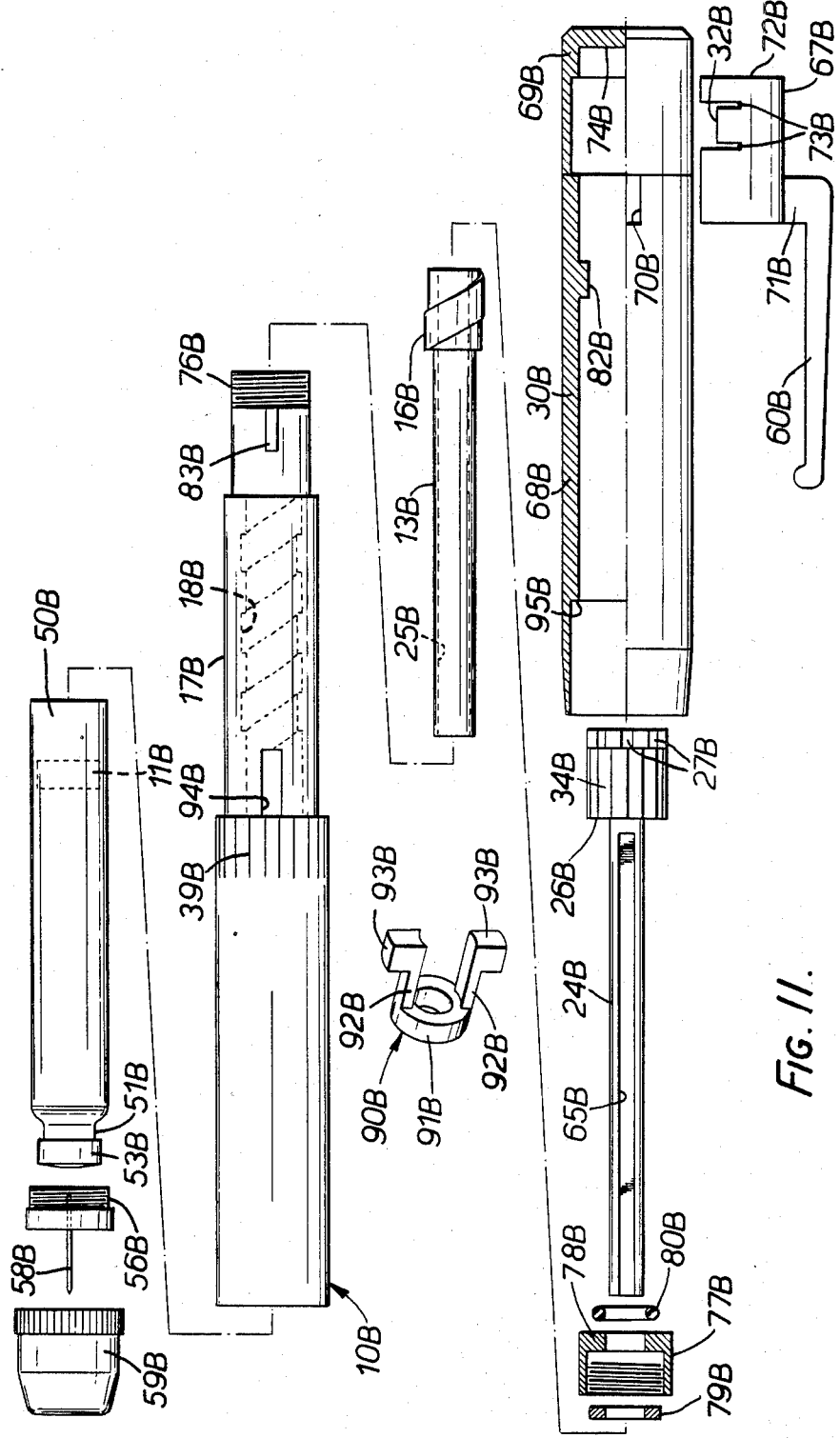
FIG. 11 is an "exploded" view of the syringe of FIGS. 9 and 10 with an ampoule.

To control the telelscopic sliding movement of the cap 30B on the barrel 10B, a reset washer 90B is provided. This comprises a ring 91B which surrounds the lower end portion of the plunger 13B within the barrel 10B and which carries two diametrically-opposite axially-forwardly extending arms 92B, one on either side of the plunger 13B. Each arm 92B has a radially-outwardly directed lug 93B which projects freely through one of two axially-extending slots 94B formed in the wall of the barrel portion 17B, respectively on opposite sides thereof, immediately below the thread 18B, as shown in FIG. 10B. Each lug 93B projects outside the barrel portion 17B and underlies an annular step 95B formed in the interior of the cap 30B. The reset washer 90B can move axially in the barrel 10B through a distance limited by the travel of the lugs 93B in the slots 94B, and when the barrel 10B does not contain an ampoule 50B the downward travel of the cap 30B is thus limited by the engagement of the lugs 93B with the lower ends of the slots 94B, in its lowered position of free rotation with the lug 82B clear of the lug 83B. However when an ampoule 50B is inserted into the lower portion of the barrel 10B through its lower end and the plug 56B replaced, the upper end of the ampoule will abut the lower face of the reset washer 90B, lifting the washer and the cap 30B and holding them in their raised position, with the lug 83B limiting the rotation of the cap 30B by its engagement with the lug 82B. Upward telescoping movement of the cap 30B on the barrel is limited by the abutment of the lug 82B against the retaining sleeve 77B on the upper end of the barrel portion 17B.

The method of operation of the syringe of FIGS. 9 to 14 will now be described. To load the syringe, the protective cap 59B and needle mounting plug 56B are removed, and a fresh ampoule 50B containing a quantity of the fluid to be injected, sufficient for a sequence of doses, is inserted through the open end of the barrel 10B remote from the cap 30B. At this stage the plunger 13B is assumed to be fully screwed into the barrel portion 17B, by the method to be described below. The inner end of the ampoule engages the reset washer 92B, and lifts it together with the cap 30B to the full-line retracted position of FIG. 10B, allowing the plug 56B to be screwed into the end of the barrel causing the needle 58B to puncture the diaphragm 52B and penetrate into the interior of the ampoule. The cap 30B is now rotated, in the clockwise direction in FIG. 14, to ensure that liquid is being expressed from the syringe and to bring the pointer 40B to the zero position on the scale 39B with the lug 82B engaged against the barrel stop 83B. The syringe is now ready for use.

To set the size of a dose to be dispensed, the cap 30B is rotated anticlockwise in FIG. 14, until the pointer 40B reaches the index mark on the scale which corresponds to the volume of the required dose. To dispense or inject this preset dose, the cap 30B is then rotated clockwise in FIG. 14 back to the zero position. This causes the ratchet cylinder 26B to be correspondingly rotated by the pawl 32B, turning the driving rod 24B and with it the plunger 13B clockwise through the same preset angle. The interengagement of the leadscrew threads 16B and 18B drives the plunger 13B axially downwardly (in FIG. 10A) through a corresponding distance and causes it to drive the ampoule plug 11B down through that distance expressing a dose of liquid through the needle 58B. The pitch of the leadscrew threads 16B and 18B and the internal diameter of the ampoule are so related to the scale 39B that the volume of the dose thus expressed through the needle equals the scale figure to which the pointer 40B was preset prior to the expression of that particular dose.

Successive metered doses, each preset in the same manner, can be expressed from the syringe until the ampoule is almost empty. During each reverse rotation of the cap 30B to preset the succeeding dose, the pawl 32B rides over the tips of the ratchet teeth, the friction between the leadscrew threads 16N and 18B, supplemented by that between the resilient O-ring 80B, the ratchet head and the retaining sleeve 77B, being sufficient to hold the plunger 13B stationary.

The length of the plunger 13B, and its distance of axial travel, are chosen so that the plug 11B approaches close to but does not abut against the inner end of the ampoule, and so that the ampoule can be almost completely emptied but will not be broken by the action of the plunger 13B and plug 11B. The barrel 10B of the syringe may either be of transparent material or be formed with longitudinal slots, and the wall of the ampoule may be of transparent or translucent material, to enable the degree of emptying of the ampoule to be checked visually in the syringe. A mark may be provided on the ampoule, or on the barrel wall, to indicate when the ampoule contains less liquid than can be expressed by one full turn of the cap 30B.

After the required sequence of doses has been expressed, or when empty, the ampoule can be removed from the syringe. The used ampoule can be provided with a replacement membrane and refilled and sealed for further use, or it can be thrown away and replaced by a fresh prefilled ampoule complete with sealing plug 11B. The needle assembly 56B, 58B can be replaced as necessary.

Before a new or refilled ampoule 50B is recharged into the barrel 10B, the plunger 13B must be screwed fully back into the upper portion 17B of the barrel. This is done simply by depressing the cap 30B into its lower (broken-line) position on the empty barrel (as shown on the right-hand side of FIGS. 10A and 10B), or ensuring that it has fallen into that position, the reset washer descending to the lower ends of the slots 94B since there is no ampoule 50B in the barrel to hold the washer at the upper ends of the slots. In this depressed position of the cap 30B, its stop lug 82B will be below the barrel stop lug 83B and the cap can turn freely. The cap is now pressed down so that its inner formations 74B engage the grooves or serrations 73B on the ratchet cylinder 26B, and is rotated in the anticlockwise direction of FIG. 14 in successive turns so as to frictionally rotate the ratchet cylinder (resting on the resilient O-ring 80B) together with the driving rod 24B and cause it to screw the plunger 13B fully back into the threaded portion 17B of the barrel. When this has been done, the insertion of a fresh ampoule into the barrel of the syringe will raise the reset washer 92B together with the cap 30B to its retracted position ready for use.

Each of the two specific embodiments described and illustrated above has the advantage that during the presetting of the metering device by rotation of the cap 30 or 30B, the number of "clicks" produced as the pawl tooth 32 or 32B rides over successive ratchet teeth 34 or 34B can be heard and counted, the count giving a numerical indication of the angle through which the cap is turned to preset the next dose. If the relationship of the ratchet tooth pitch to the corresponding displacement of liquid by the piston on the plug 11, 11B is known, the count of "clicks" enables the user to determine aurally the volume of the next dose to which the device is being preset. This is beneficial for operation of the syringe by blind or poorly-sighted persons such as diabetic patients using the syringe for self-injection of insulin.

Figure 15:
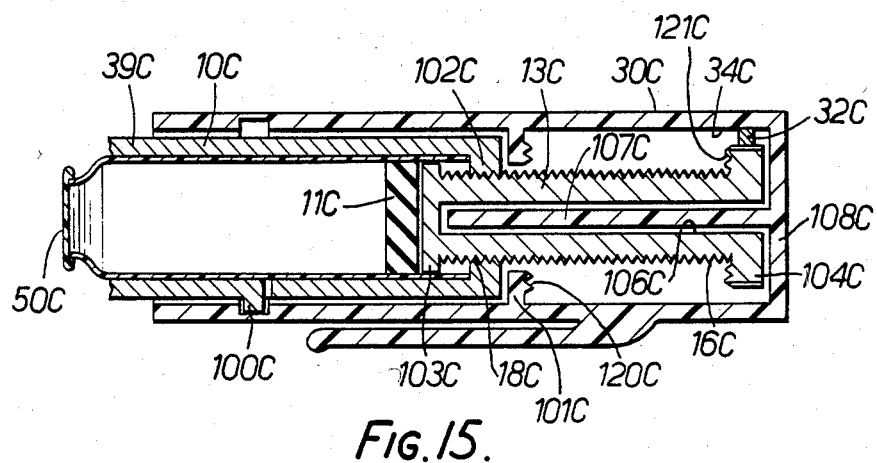
FIG. 15 is a longitudinal sectional view of a third embodiment of the invention.
Figure 16:
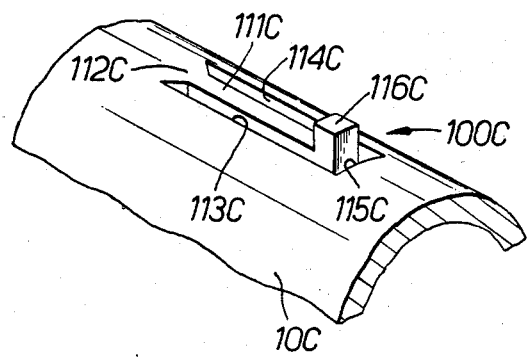
FIG. 16 is a perspective view on a larger scale showing the spring catch on the cylinder barrel of the embodiment of FIG. 15.
Figure 17:
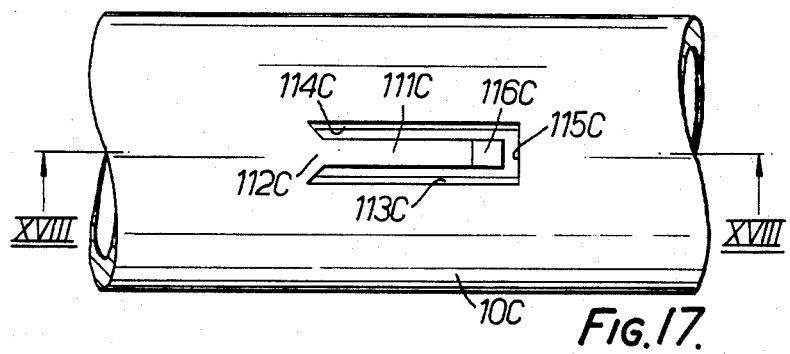
FIG. 17 is a fragmentary plan view of the portion of the barrel containing the spring catch.

FIGS. 15 to 19 show another embodiment of the invention, in which the construction of the left-hand end of the syringe, not shown in FIG. 15, is the same as in that of FIGS. 9 to 14, a protective cap and needle-mounting screw plug similar to the items 59B and 56B being removable from the open left-hand end of the cylinder barrel, not shown in FIG. 15, to allow the insertion and removal of an ampoule containing dose fluid. In the embodiment of FIGS. 15 to 19, parts which correspond to parts of the embodiment of FIGS. 9 to 14 are given the same reference numerals as in that embodiment but identified by the letter C.

In the embodiment of FIG. 15 the syringe cylinder barrel 10C carries a rotatable operating cap 30C normally retained against axial displacement by a spring catch 100C to be described. In addition to the spring catch 100C, axial sliding movement of the cap 30C to the left in FIG. 15 is prevented by an internal radial flange 101C formed integrally with the cap and arranged to abut the right-hand radial end face of the cylinder barrel 10C. The external screwthread 16C of the plunger 13C is threaded through a cooperating internal screwthread 18C in the central aperture of the end flange 102C of the barrel 10C, and the plunger 13C has an enlarged-diameter head 103C on its left-hand end as seen in FIG. 15, which approximately matches the diameter of the sliding rubber plug 11C within an ampoule 50C which it engages in use. The enlarged head 103C also prevents the plunger 13C from being completely unscrewed from the barrel. At its other end the plunger 13C carries a second enlarged head 104C on which a pawl 32C in the form of a spring steel strip is mounted. Although in FIG. 15 the two heads are shown as being integral with the plunger for convenience, in practice one of the two heads 103C and 104C would be a separate member suitably secured to the shank of the plunger in assembly, after the threading of the plunger into the barrel screwthread 18C.

The pawl 32C cooperates with longitudinal grooves (not shown) formed in the internal cylindrical surface of the cap 30C, between the flange 101C and the right-hand end of the cap as seen in FIG. 15, to form with the longitudinally grooved surface a unidirectional ratchet coupling. The cap 30C is made of a plastics material, for example acrylonitrile butadiene styrene, having a suitable hardness to provide appropriate resistance to wear and shaped so as to allow the tip of the pawl 32C to cooperate with its grooved cylindrical internal surface when the cap is rotated in the direction tending to screw the plunger 13C further into the barrel. This locking action transmits the rotational drive of the cap 30C to the plunger 13C so that the plunger is positively rotated by the cap. When the cap is turned in the opposite direction, however, the shape of the grooves is such as to permit the internal surface of the cap to slide over the tip of the pawl without driving the plunger. This arrangement also provides for an audible "click" mechanism as in the earlier embodiments enabling poorly sighted patients to count the size of the dose. The plunger 13C is also provided with an axial bore 106C extending from its right-hand end in FIG. 15 almost throughout its entire length, and an elongate coaxial integral spigot 107C on the end wall 108C of the cap is a free sliding fit in the bore 106C to provide support for the cap on the plunger.

The catch 100C referred to not only holds the cap 30C on the barrel 10C against axial sliding but also provides a removable stop which limits the rotation of the cap to just under 360°, the stop being held in its operative position by the side of an ampoule 50C when inserted in the cylinder barrel 10C. Thus as shown in detail in FIGS. 16 to 19, the catch 100C comprises a resilient tongue 111C integral with the wall of the cylinder barrel 10C at one end 112C and defined by a pair of parallel slots 113C, 114C in the barrel wall which are joined around the other, free end of the tongue 111C by a yoke slot 115C. The free end of the tongue 111C carries an integral upstanding head 116C. The tongue is resiliently biassed in manufacture so that it tends to spring radially inwardly of the barrel wall into the broken line position shown in FIG. 18, in which position its head 116C lies within the external circumferential surface of the barrel. However, when an ampoule 50C is inserted into the barrel 10C, its side wall bears against the tongue 111C to press it outward against its bias into the position shown in firm lines in FIGS. 16, 18 and 19 in which its head protrudes outside the external surface of the barrel 10C and into engagement in a circumferential groove 118C formed in the internal surface of the cap 30C, so as to retain the cap axially on the barrel 10C whilst allowing rotation of the cap. The groove 118C is interrupted at one point in its circumference, by an integral lug 119C (FIG. 19) formed to the full wall thickness of the cap, and the lug 119C cooperates with the protruding head 116C to form a stop means which limits the possible rotation of the cap on the barrel to a little less than 360°. One limiting angular position of the cap is at the zero position of the angular scale (not shown) which is marked circumferentially on the exterior of the barrel in the region marked 39C in FIG. 15, for cooperation with a pointer marked on the cap.

Thus with this embodiment, when an ampoule 50C is in position it holds the spring catch 100C in its engaged position, with the tongue head 116C engaged in the groove 118C to prevent the cap sliding axially on the barrel. The cap 30C can be rotated on the barrel away from the zero position on the scale to preset a dose, the pawl 32C sliding around the interior of the cap, and when expression of the preset metered dose is required, the cap is simply rotated in the opposite direction towards the zero position, rotating the plunger 30C as the pawl 32C engages with a longitudinal groove in the internal surface of the cap, and so causing the plunger to be screwed forwards through the corresponding distance to express the preset dose. Rotation of the cap is stopped in the zero scale position by the engagement of the lug 119C against the side of the tongue head 116C protruding into the groove 118C.

Figure 18:
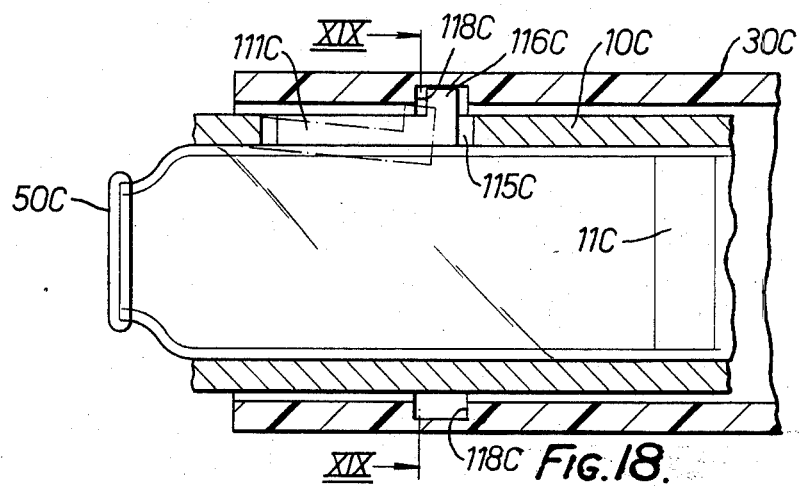
FIGS. 18 and 19 are respectively views in section on the lines XVIII—XVIII and XIX—XIX of FIG. 17.
Figure 19:
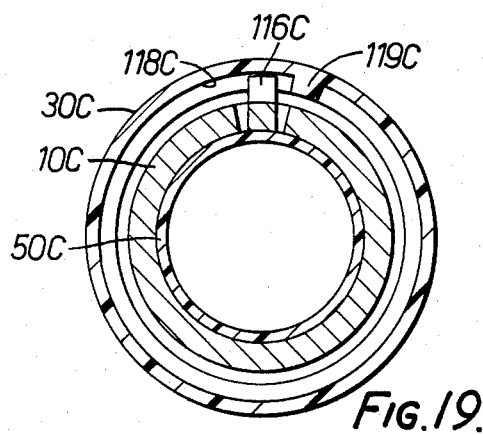

When after successive expression of a series of doses the ampoule is empty and is removed from the cylinder barrel 10C, the tongue 111C is free to spring inwardly to its broken-line position in FIG. 18 so that the cap 30C is freed to slide axially along the barrel 10C. The cap is now pulled outwardly along the barrel until serrated formations or a friction surface 120C on the side of its internal flange 101C engage with cooperating formations or a cooperating friction surface 121C formed on the inner radial face of the plunger head 104C, this engagement enabling the plunger 13C to be screwed fully back to its starting position in the barrel simply by the rotation of the cap 30C. When this has been done the cap 30C is pushed back along the barrel until its flange 101C engages the end of the barrel, riding over the catch 100C. The insertion of a fresh ampoule into the cylinder barrel 10C will lift the tongue 111C so that its head 116C again protrudes into the groove 118C in the cap to retain the cap in its operating axial position.

It will be appreciated that in each of the specific embodiments described and illustrated, the presetting of each dose is effected by the rotation of the operating member, i.e. the cap 30, through a selected angle measured on an angular scale, the corresponding axial displacement of the plunger in the next operating stroke, and hence the volume of fluid expressed, being controlled by the associated screw mechanism in accordance with the pitch angle of the interengaged screwthreads. Thus a very fine presetting adjustment with a high degree of definition in the angular scale is made available by virtue of this rotary screw presetting arrangement.

We claim:

1. A dose metering device for a syringe having a cylinder in which a piston moves to express liquid therefrom, which device comprises an axially-movable plunger which is adapted in use to drive the piston axially in the cylinder for dose expression therefrom, a manually-rotatable operating member, a rotary screw mechanism operatively associated with the plunger, a unidirectional coupling by which the operating member is operatively coupled to the rotary screw mechanism, angular rotation of the operating member in one direction (referred to as the forward direction) being transmitted by the unidirectional coupling to the rotary screw mechanism which is arranged to convert said transmitted rotation into corresponding axial movement of the plunger, whereby in use successive rotary operating strokes of the operating member in the said forward direction are converted into successive axial movement steps of the plunger to express successive doses from the syringe whose volumes correspond to the angular extents of the respective operating strokes of the operating member, and stop means arranged to limit each of the said operating strokes of the operating member at the same predetermined angular finishing point, the unidirectional coupling permitting the manual angular retraction of the operating member independently of the plunger after each said operating stroke from its finishing point predetermined by the stop means to a selected angular position constituting a variable starting point for the next operating stroke, and scale means arranged to indicate selectable angular positions of a plurality of said starting points, whereby the volume of each dose to be expressed is variably preset in use by selection of the angular position, as indicated by the scale means, of the starting point of the respective operating stroke of the operating member.

2. A device as claimed in claim 1, in which the scale means comprises an arcuate scale of indicia and a cooperating pointer, by which the angular extent of each operating stroke from its selected starting point to the finishing point determined by the stop means can be measured directly on the scale, from which measurement the volume of the corresponding dose is ascertainable, the operating member being rotatable into a position in which the pointer indicates the selected starting point on the scale.

3. A device as claimed in claim 1 or claim 2, in which the scale means is calibrated in units of dose volume.

4. A device as claimed in claim 1 or claim 2, in which the screw mechanism comprises an external helical screwthread formed coaxially on the plunger and a cooperating internal helical screwthread formed in a part which in use is fixed to the cylinder, the plunger being rotatable relative to the cylinder.

5. A device as claimed in claim 4, in which the operating member is coupled coaxially to the plunger through the said unidirectional coupling and screw mechanism.

6. A device as claimed in claim 5, in which the operating member is coupled coaxially through the unidirectional coupling to a rotary driving member keyed to the threaded plunger for coaxial rotation therewith but axially slidable relative thereto.

7. A device as claimed in claim 6, in which the threaded plunger comprises a tubular member having an axial bore, and the rotary driving member is an elongate member extending slidably within said bore and keyed to the plunger for rotation therewith.

8. A device as claimed in claim 1 or claim 2, in which the unidirectional coupling is a ratchet and pawl mechanism.

9. A device as claimed in claim 7, in which the unidirectional coupling is a ratchet and pawl mechanism whereof the ratchet comprises a toothed wheel secured coaxially to the rotary driving member and the cooperating pawl is carried by the operating member.

10. A device as claimed in claim 1 or claim 2, in which the stop means comprises a stop member carried by a part of the device which in use is atached to the cylinder of a syringe, and a cooperating abutment on the operating member which is adapted to engage the stop at the end of each operating stroke.

11. A device as claimed in claim 10 in which the stop member is a fixed stop.

12. A device as claimed in claim 11 in which the stop member is detachably mounted on the said part and in which the abutment is formed in a pointer constituting a part of the scale means and carried by the operating member.

13. A device as claimed in claim 1 or claim 2, in which the stop means includes a fixed stop.

14. A device as claimed in claim 7, in which the said tubular member is adapted to be detachably secured to the cylinder of a syringe, and carries a stop member.

15. A device as claimed in claim 14, in which the stop member forms part of a releasable connection between said tubular member and the cylinder.

16. A device as claimed in claim 1 or claim 2, in combination with a syringe having a cylinder to which said device is attached and a piston arranged to be acted on by the plunger of said device for dose expression.

17. A syringe including a cylinder and a piston movable axially in said cylinder to express liquid therefrom, an axially-movable plunger arranged and adapted to drive the piston for expression of a dose of liquid, a manually-rotatable operating member, a rotary screw mechanism operatively associated with the plunger, a unidirectional coupling by which the operating member is operatively coupled to the rotary screw mechanism, angular rotation of the operating member in one direction (referred to as the forward direction) being transmitted by the unidirectional coupling to the rotary screw mechanism which is arranged to convert said transmitted rotation into corresponding axial movement of the plunger whereby in use successive rotary operating strokes of the operating member in the said forward direction are converted into successive axial movement steps of the plunger to express successive doses from the syringe whose volumes correspond to the angular extents of the respective operating strokes of the operating member, and stop means arranged to limit each of the said operating strokes of the operating member at the same predetermined angular finishing point, the unidirectional coupling permitting the manual angular retraction of the operating member independently of the plunger after each said operating stroke from its finishing point predetermined by the stop means to a selected angular position constituting a variable starting point for the next operating stroke, and scale means arranged to indicate selectable angular positions of a plurality of said starting points, whereby the volume of each dose to be expressed is variably preset in use by selection of the angular position, as indicated by the scale means, of the starting point of the respective operating stroke of the operating member.

18. A syringe as claimed in claim 17, in which the scale means comprises an arcuate scale of indicia and a cooperating pointer by which the angular extent of each operating stroke from its selected starting point to the finishing point determined by the stop can be measured directly on the scale, from which measurement the volume of the corresponding dose is ascertainable, the operating member being rotatable into a position in which the pointer indicates the selected starting point on the scale.

19. A syringe as claimed in claim 18, in which the scale is calibrated in units of dose volume.

20. A syringe as claimed in any one of claims 17 through 19, in which the said screw mechanism comprises an external helical screwthread formed coaxially on the plunger and a cooperating internal helical screwthread formed in the cylinder, the plunger being rotatable in the cylinder by said operating member acting through the unidirectional coupling.

21. A syringe as claimed in claim 20, in which the operating member is coupled coaxially to the plunger through the said unidirectional coupling and screw mechanism.

22. A syringe as claimed in claim 21, which includes a rotary driving member to which the operating member is coaxially coupled by the unidirectional coupling, the rotary driving member being keyed to the threaded plunger for coaxial rotation therewith but being axially slidable relative thereto.

23. A syringe as claimed in claim 22, in which the threaded plunger comprises a tubular member having an axial bore, and in which the rotary driving member is an elongate member extending slidably within said bore and keyed to the plunger for rotation therewith.

24. A syringe as claimed in claim 23, in which said unidirectional coupling comprises a ratchet and pawl mechanism whereof the ratchet comprises a toothed wheel secured coaxially to the rotary driving member and the cooperating pawl is carried by the operating member.

25. A syringe as claimed in any one of claims 17 through 19, wherein the stop means comprises a stop member carried by the cylinder of the syringe, and a cooperating abutment on the operating member adapted and arranged to engage the stop member at the end of each operating stroke.

26. A syringe as claimed in claim 25, wherein the stop member is a fixed stop.

27. A syringe as claimed in any one of claims 17 through 19, in which the unidirectional coupling comprises a ratchet and pawl mechanism.

28. A syringe as claimed in any one of claims 17 through 19, in which the cylinder is adapted to receive and directly contain a quantity of the dose of liquid sealed in the cylinder by the piston which is a close sliding fit in the piston.

29. A syringe as claimed in any one of claims 17 through 19, in which the cylinder is adapted to hold an ampoule prefilled with a quantity of the dose liquid, the piston being arranged and adapted to express liquid from a said ampoule in the cylinder when the piston is advanced along the cylinder during an operating stroke of the operating member.

30. A syringe as claimed in claim 29, in which a piston of the syringe is contained in the prefilled ampoule and seals said quantity of dose liquid therein, the piston being a close sliding fit within the interior of the ampoule.

31. A syringe as claimed in claim 29, including a tubular needle mounted in the cylinder and arranged to pierce the wall of the ampoule to allow dose liquid to be expressed therefrom through the needle during an operating stroke of the operating member.

32. A syringe as claimed in claim 29, in which the operating member comprises a sleeve rotatably mounted on the exterior of the cylinder and slidable thereon between a first and a second longitudinal position thereon, and in which the stop means includes a stop mounted on the cylinder and a cooperating abutment on the sleeve, the abutment engaging with the stop to limit the rotation of the sleeve when the sleeve is in the said first longitudinal position, but the abutment being movable clear of the stop by sliding movement of the sleeve into the said second longitudinal position wherein the stop no longer hinders the free rotation of the sleeve on the cylinder.

33. A syringe as claimed in claim 32, in which the sleeve is arranged to be held in its said first longitudinal position by an ampoule inserted into the cylinder, and to be free to move into its said second longitudinal position when the ampoule is removed from the cylinder.

34. A syringe comprising a cylinder and a piston movable axially in the cylinder for the expression of dose liquid therefrom, an internal helical screwthread formed on the surface of the cylinder, an elongate plunger in the cylinder arranged to act on the piston, an external helical screwthread formed on the plunger, said internal and external screwthreads being in threaded relationship whereby a rotation of the plunger about its longitudinal axis is converted into a corresponding axial movement of the plunger and piston for expressing a dose, a rotary driving member keyed to the plunger for coaxial rotation therewith, the plunger being longitudinal slidable relative to the rotary driving member, a manual operating member rotatably mounted coaxially on the cylinder, a ratchet and pawl mechanism acting between the operating member and the rotary driving member whereby an angular rotation of the operating member in a first angular direction is transmitted to the rotary driving member and thence to the plunger to cause the plunger to advance the piston a corresponding axial distance so as to express a dose whose volume corresponds to the angle through which the operating member is rotated, stop means adapted and arranged to limit the rotation of the operating member in the said first angular direction at a predetermined finishing position, the ratchet and pawl mechanism permitting the manual rotation of the operating member in the direction opposite to the said first angular direction from the predetermined finishing point to a variably-selected starting position for a subsequent dose expression, and scale means arranged to indicate a plurality of selectable starting positions, whereby the volume of each dose to be expressed from the syringe is variably preset in use by selection of the angular starting point, indicated on the scale means, to which the operating member is rotated prior to its rotation towards the finishing point for the expression of that dose.

35. A syringe as claimed in claim 34, in which the scale means is calibrated in units of dose volume whereby the volume of each dose to be expressed is readable directly by reading the position of the corresponding said starting point selected on the scale.

36. A syringe as claimed in claim 34 or claim 35, in which the scale means comprises an arcuate scale of indicia and a cooperating pointer, one on the sleeve and the other on the cylinder.

37. A syringe as claimed in claim 34 or 35, in which the operating member comprises a sleeve rotatably mounted on the exterior of the cylinder and slidable thereon between a first and a second longitudinal position, and in which the stop means includes a stop mounted on the cylinder and a cooperating abutment on the sleeve, the abutment engaging with the stop means to limit the rotation of the sleeve when the sleeve is in the said first longitudinal position, but the abutment being movable clear of the stop by sliding movement of the sleeve into the said second longitudinal position wherein the stop no longer hinders the free rotation of the sleeve on the cylinder.

38. A syringe as claimed in claim 37, in which the cylinder is adapted to hold an ampoule prefilled with a quantity of dose liquid sealed in the ampoule, and in which the sleeve is arranged to be held in its said first longitudinal position by an ampoule inserted into the cylinder and to be free to move into its second longitudinal member when the ampoule is removed from the cylinder.

39. A syringe as claimed in claim 38, including a detent member slidably mounted in the cylinder and having a portion extending through a longitudinal aperture slot formed in the wall of the cylinder, the detent member being arranged to engage at one end outside the cylinder with the sleeve and to be engaged at its other end within the interior of the sleeve by an ampoule inserted into the cylinder, the ampoule when fully inserted causing the detent member to hold the sleeve in its said first longitudinal position, and the detent being slidable when the ampoule is removed to allow the sleeve to be moved into its said second longitudinal position.

40. A syringe comprising a cylinder, a piston movable axially in the cylinder for the expression of dose liquid therefrom, an internal helical screwthread formed in the cylinder, an elongate plunger in the cylinder arranged to act on the piston, an external helical screwthread formed on the plunger, said internal and external screwthread being in threaded relationship whereby a rotation of the plunger about its longitudinal axis is converted into a corresponding axial movement of the plunger and piston for expressing a dose, a manual operating sleeve rotatably mounted coaxially on the cylinder, a ratchet and pinion mechanism arranged to transmit a rotation of the operating sleeve in a first angular direction to the threaded plunger to cause the plunger to advance the piston a corresponding axial distance so as to express a dose whose volume corresponds to the angle through which the operating sleeve is rotated, stop means adapted and arranged to limit the rotation of the operating sleeve in the said first angular direction at a predetermined finishing point, the ratchet and pawl mechanism permitting the manual rotation of the operating sleeve in the said first angular direction from the predetermined finishing point to a variably-selected starting point for a subsequent dose expression, and scale means arranged to indicate a plurality of selectable starting points, whereby the volume of each dose to be expressed from the syringe is variably preset in use by selection of the angular starting point, indicated on the scale means, to which the operating sleeve is rotated prior to its rotation towards the finishing point for the expression of that dose.

41. A syringe as claimed in claim 40, in which the scale means is calibrated in units of dose volume whereby the volume of each dose to be expressed is readable directly by reading the position of the corresponding said starting point selected on the scale.

42. A syringe as claimed in claim 40 or claim 41, in which the ratchet and pawl mechanism comprises a toothed ratchet formation formed circumferentially around and in the internal wall surface of the sleeve, and a cooperating pawl carried by the plunger.

43. A syringe as claimed in claim 40 or claim 41, in which the operating sleeve is longitudinally slidably on the cylinder, and in which the stop means comprises a movable stop member carried by the cylinder and held in an operative position in which it is entered into a circumferential groove formed in and around the inner surfaces of the wall of the sleeve so as to retain the sleeve in an operative longitudinal position on the cylinder, in which operative longitudinal position the sleeve is rotatable for dose expression, the sleeve having an abutment arranged to engage the stop member and limit the rotation of the sleeve in the said predetermined finishing position when the stop member is entered in the groove, and in which the stop member is retractable from the groove to allow the sleeve to be slid longitudinally off the cylinder.

44. A syringe as claimed in claim 43, in which the cylinder is adapted to hold an ampoule prefilled with a quantity of dose liquid sealed in the ampoule by a piston of the syringe which is a sliding fit in the interior of the ampoule, and in which the movable stop is resiliently biassed away from its operative position entered in the groove, but is arranged to be held in said operative position by an ampoule when inserted into the cylinder.

* * * * *

UNITED STATES PATENT AND TRADEMARK OFFICE
CERTIFICATE OF CORRECTION

PATENT NO. : 4,498,904

DATED : February 12, 1985

INVENTOR(S) : Robert C. Turner

It is certified that error appears in the above-identified patent and that said Letters Patent is hereby corrected as shown below:

On the title page the following should be added:

--[30] FOREIGN/PCT APPLICATIONS-UNITED KINGDOM  8104323
       Filed 02/12/82
       PCT/GB82/00034  Filed 02/12/82  --

Signed and Sealed this

Eleventh Day of June 1985

[SEAL]

Attest:

DONALD J. QUIGG

Attesting Officer

Acting Commissioner of Patents and Trademarks

UNITED STATES PATENT AND TRADEMARK OFFICE
CERTIFICATE OF CORRECTION

PATENT NO. : 4,498,904

DATED : February 12, 1985

INVENTOR(S) : Turner

It is certified that error appears in the above-identified patent and that said Letters Patent is hereby corrected as shown below:

THE PRIORITY DATA INFORMATION IS INCORRECT; SHOULD READ AS FOLLOWS:

--[30] Foreign/PCT Applications
United Kingdom     8104323     February 12, 1981
PCT/GB82/0034   2/12/82

This certificate supersedes certificate of correction issued June 11, 1985.

Signed and Sealed this

Nineteenth Day of November 1985

[SEAL]

Attest:

Attesting Officer

DONALD J. QUIGG

Commissioner of Patents and Trademarks